United States Patent
Daglow et al.

(10) Patent No.: US 8,140,163 B1
(45) Date of Patent: Mar. 20, 2012

(54) IMPLANTABLE PULSE GENERATOR AND METHOD OF USE

(75) Inventors: Terry D. Daglow, Allen, TX (US); Robert E. Jones, McKinney, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 385 days.

(21) Appl. No.: 12/471,969

(22) Filed: May 26, 2009

Related U.S. Application Data (60) Provisional application No. 61/055,655, filed on May 23, 2008.

(51) Int. Cl.
*A61N 1/00* (2006.01)

(52) U.S. Cl. .......................................... 607/36

(58) Field of Classification Search .................. 439/909; 607/36, 119
See application file for complete search history.

(56) References Cited

U.S. PATENT DOCUMENTS

| | | | |
|---|---|---|---|
| 6,198,969 B1 | 3/2001 | Kusma | |
| 6,321,126 B1 * | 11/2001 | Kuzma | 607/137 |
| 6,741,892 B1 | 5/2004 | Meadows et al. | |
| 6,895,276 B2 | 5/2005 | Kast et al. | |
| 7,083,474 B1 | 8/2006 | Fleck et al. | |
| 7,244,150 B1 | 7/2007 | Brase et al. | |
| 7,590,451 B2 | 9/2009 | Tronnes et al. | |
| 7,798,864 B2 | 9/2010 | Barker et al. | |
| 2005/0027326 A1 | 2/2005 | Ries et al. | |
| 2005/0245982 A1 | 11/2005 | Kast et al. | |
| 2009/0247018 A1 | 10/2009 | Kast et al. | |

* cited by examiner

*Primary Examiner* — George Manuel
*Assistant Examiner* — Robert Wieland
(74) *Attorney, Agent, or Firm* — Christopher S. L. Crawford; Craig Hoersten; Peter R. Lando (57) ABSTRACT

In one embodiment, there is disclosed an implantable pulse generator for electrically stimulating a patient, which comprises: a housing enclosing pulse generating circuitry; a header coupled to the metallic housing, the header including an inner guide having cylindrical passages for accepting feedthrough wires such that the inner guide is slidingly coupled to the plurality of feedthrough wires, wherein the inner guide has an exterior surface which intersects a portion of each cylindrical passage to create an exposed portion of each feedthrough wire, an outer seal having an interior surface sized to support terminals against the exposed portion of the feedthrough wires, and an outer clip component fitting over at least a portion of the outer seal component.

22 Claims, 6 Drawing Sheets

IMPLANTABLE PULSE GENERATOR AND METHOD OF USE

CROSS-REFERENCE TO RELATED APPLICATIONS

This application claims the benefit of U.S. Provisional Application No. 61/055,655, filed May 23, 2008, which is incorporated herein by reference.

TECHNICAL FIELD

The present application is generally related to neurostimulation equipment used in the medical field, and in particular to header components of implantable pulse generators.

BACKGROUND INFORMATION

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. Other examples include deep brain stimulation, cortical stimulation, cochlear nerve stimulation, peripheral nerve stimulation, vagal nerve stimulation, sacral nerve stimulation, etc. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or more leads. The pulse generator is typically implemented using a metallic housing that encloses circuitry for generating the electrical pulses, control circuitry, communication circuitry, a rechargeable battery, etc. The pulse generation circuitry is electrically coupled to one or more stimulation leads through electrical connections provided in a "header" of the pulse generator. Typically, conductors in the leads carry the electrical pulses from a longitudinal series of annular terminals which are inserted into the header to a longitudinal series of stimulation electrodes implanted at the tissue site.

Pulse generators are preferably small to limit patient trauma and discomfort. Similarly, smaller headers used in such pulse generators are also desirable. In some circumstances, however, the overall length of the headers may be determined by the number and longitudinal spacing of the electrical connections coupling the terminals to wires coupled to the electrical circuitry within the pulse generator. It is desirable to reduce the size and spacing of the electrical connections so that either more conductors may be used or the size of the header may be reduced.

Furthermore, the placement of the electrical connectors in such a header can be unduly difficult especially when the electrical connectors are small. It is also desirable to maintain a watertight seal which will keep body fluids out of the header and between the electrical/mechanical interface of individual electrical circuits or connections.

SUMMARY

In one embodiment, there is disclosed an implantable pulse generator for electrically stimulating a patient, which comprises: a housing enclosing pulse generating circuitry; a header coupled to the metallic housing, the header including an inner guide having cylindrical passages for accepting feedthrough wires such that the inner guide is slidingly coupled to the plurality of feedthrough wires, wherein the inner guide has an exterior surface which intersects a portion of each cylindrical passage to create an exposed portion of each feedthrough wire, an outer seal having an interior surface sized to support terminals against the exposed portion of the feedthrough wires, and an outer clip component fitting over at least a portion of the outer seal component.

In another embodiment, there is disclosed a method of fabricating an implantable pulse generator which includes: providing pulse generating circuitry within a housing; providing feedthrough wires to permit electrical access to the pulse generating circuitry within the housing; coupling the feedthrough wires to an inner guide to maintain the position of the wires in such a manner that a portion of each wire is exposed, coupling the exposed portions of the feedthrough wires to corresponding connecting terminals of one or more stimulation leads, wherein the connecting terminals are held in place by respective recesses in an inner surface of an exterior seal; and placing an outer shield component over the exterior seal, the outer shield component fitting over at least a portion of the inner compliant component.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Some representative embodiments are directed to a header design for a neurostimulation system. In one embodiment, the header design might incorporate an inner guide having cylindrical passages for accepting feedthrough wires such that the inner guide is slidingly coupled to the plurality of feedthrough wires. In some embodiments, the inner guide has an exterior surface which intersects a portion of each cylindrical passage to create an exposed portion of each feedthrough wire. An outer seal may surround the inner guide and may have an interior surface sized to support terminals of a lead against the exposed portion of the feedthrough wires. In some embodiments, there may be an outer clip component fitting over at least a portion of the outer seal component.

Figure 1:
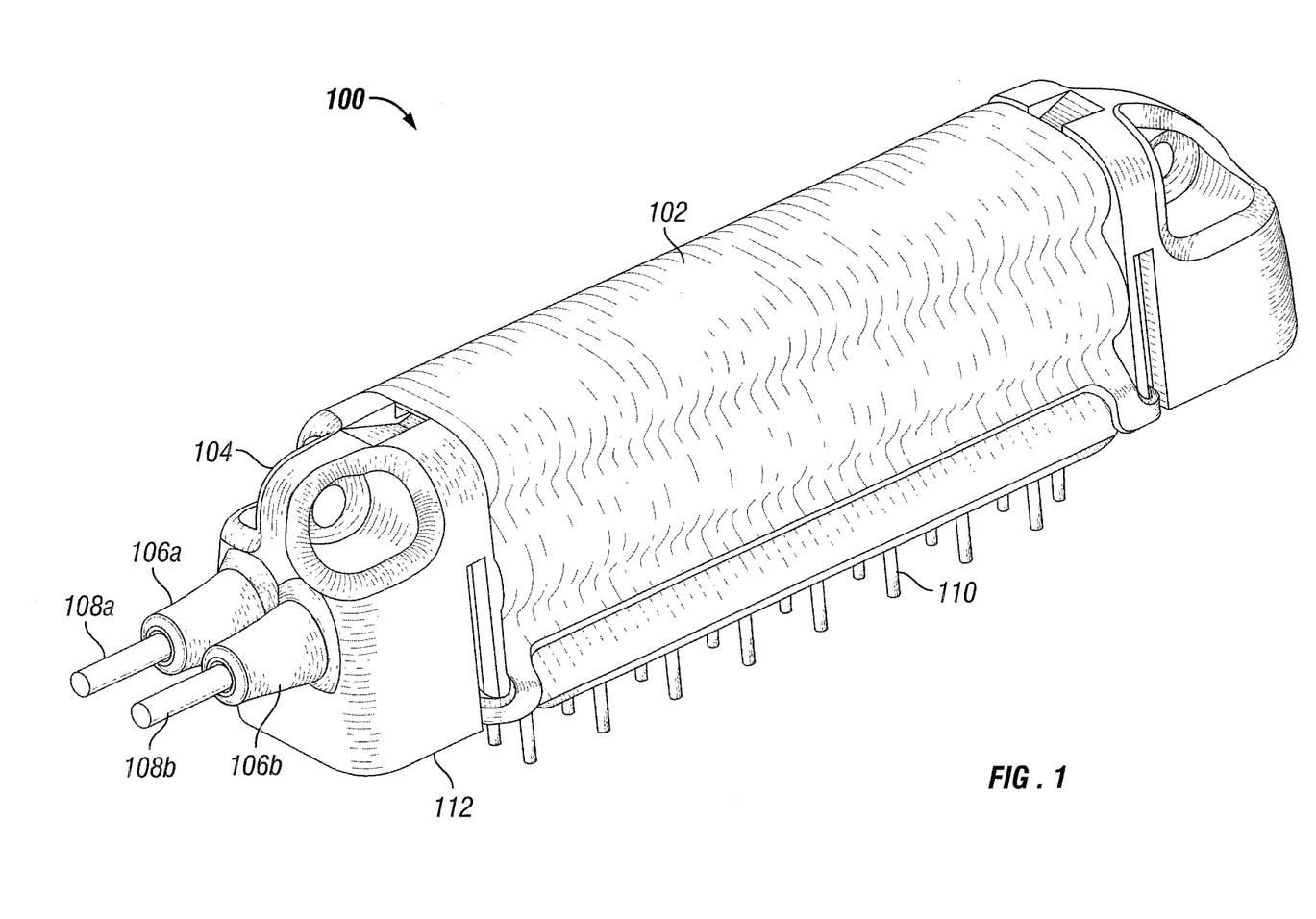
FIG. 1. is an isometric view of a header assembly for an implantable pulse generator which incorporates one or more aspects of the present invention.

Turning now to FIG. 1, there is presented an isometric view of one embodiment of a header 100 In this illustrative embodiment, the header 100 has an outer shield or clip component 102 partially covering a relatively compliant outer seal 104. In certain embodiments, the outer seal 104 may be injection molded from a biocompatible compliant material, such silicone rubber.

The clip component 102 may be fabricated from a relatively hard material to prevent damage to or puncture of the outer seal 104, such as titanium or stainless steel. In certain embodiments, the clip component 102 may also function as a biasing member and may be shaped in a manner to provide compression forces to the outer seal 104 when the clip component is coupled to the outer seal as illustrated in FIG. 1. Additionally, if a sharp object used during the implantation procedure were to contact the outer seal 104 directly, the relatively compliant material of the outer seal could be punctured somewhat easily. The puncture could allow entry of body fluids and cause the patient to experience electrical stimulation in the subcutaneous implantation pocket. By utilizing a suitable material for clip component 102, the outer seal 104 may be somewhat protected from sharp surgical tools, needles, staples, and the like.

In certain embodiments, the outer seal 104 may have two strain relief ports 106a and 106b which are adapted to receive proximal ends of stimulation leads 108a and 108b in a side-by-side manner (only portions of the stimulation leads 108a and 108b are illustrated in FIG. 1). Other embodiments may be configured to receive the stimulation leads in an above-below manner or even in an array-like manner if several stimulation leads are coupled to the header.

A plurality of feed-through wires 110 protrude from a connecting side 112 of the header 100. In certain embodiments, the feed-through wires 110 may be made from a conducting material which does not readily form an oxide film on exterior surfaces. Such conducting materials could include platinum and platinum-iridium alloys. The lack of oxide film on the feed through wires allows an electrical connection with relatively small contact forces. As will be explained in detail below, when terminals 146a-146b are inserted into the strain relief ports 106a and 106b, proximal end portions (not shown in FIG. 1) of the plurality of feed-through wires 110 contact corresponding terminals of the stimulation leads 108a and 108b within the header 100. Distal end portions of the feed-through wires 110 couple to electric circuitry of a pulse generation source, such as an implantable pulse generator ("IPG") (not shown in FIG. 1). Thus, an electrical connection is made from the electric circuitry of the pulse generation source to the stimulation leads. (For ease of explanation in this specification, the direction towards the connecting side 112 or the IPG side of the header will be defined or referred to as the distal direction and the opposing direction will be defined as the proximal direction.)

Figure 2:
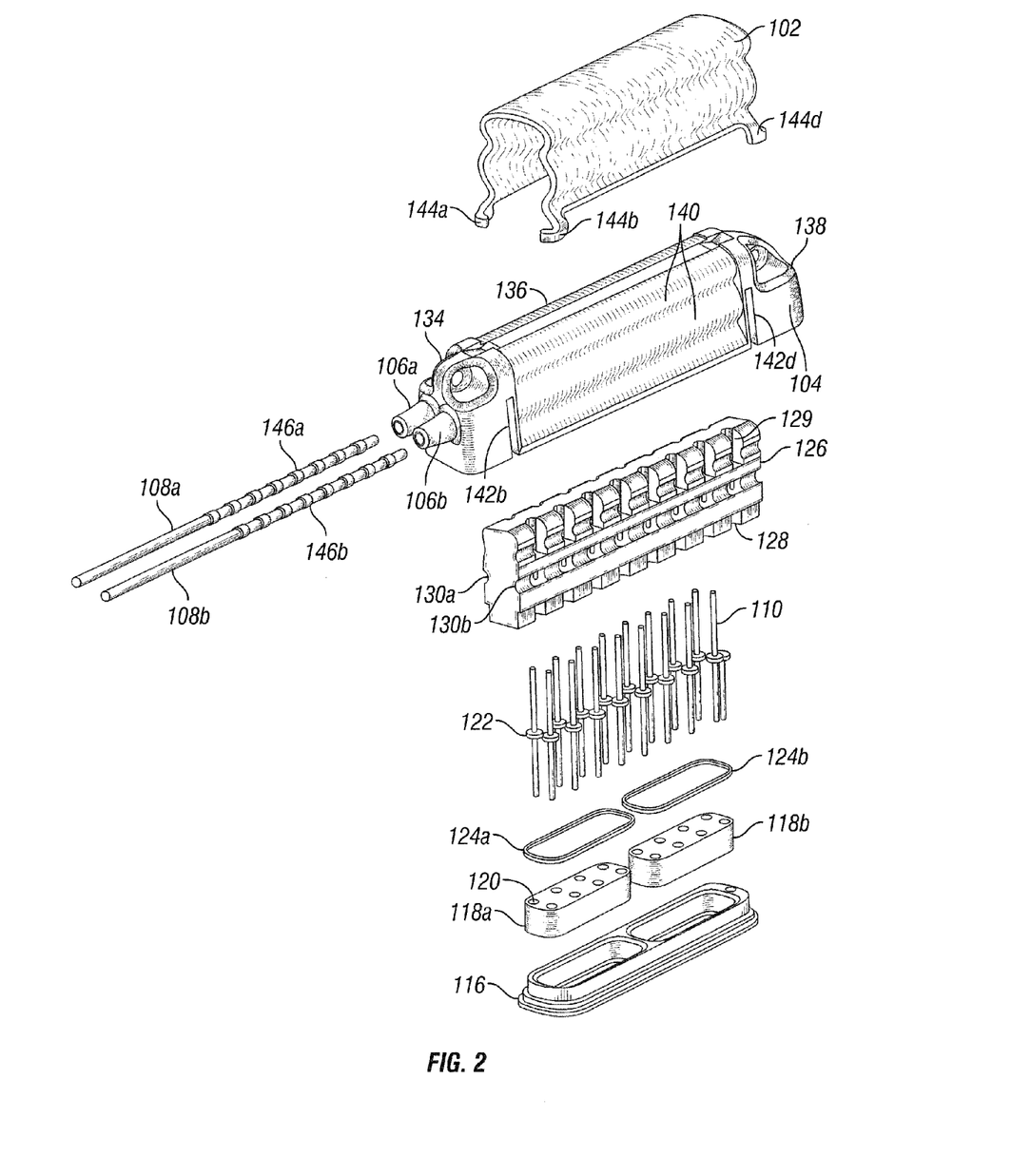
FIG. 2 is an exploded isometric view of the header of FIG. 1.

Details of the header 100 will be discussed with reference to FIG. 2, which is an exploded isometric view of the header 100. As can be seen in FIG. 2, in the illustrated embodiment, there may be a feed through base 116, which in certain embodiments may be glued or mechanically attached to an IPG (not shown in FIG. 2). In certain embodiments, the feed through base 116 may shaped to house a plurality of supports 118a and 118b arranged longitudinally within the feed through base 116. In certain embodiments, the supports 118a and 118b may be made of ceramic and may have a plurality of cylindrical passages or bores 120 which allow the feed-through wires 110 to extend through (e.g., a cylindrical shaped hole). On the proximal face of the supports 118a-118b, the diameter of the bores may be enlarged to house a plurality of wire seals 122 which may be coupled to the feed-through wires 110. In certain embodiments, there may also be base seals 124a and 124b which fit between the feed-through base 116 and the supports 118a and 118b to form seals between the supports and the feed through base. Structures 122, 124a and 124b are brazing rings, commonly known for making a hermetic seal in with feedthroughs in IPGs. Base 116 is then laser welded to the IPG can to complete the hermetic sealing of the electronics from the body fluids.

An inner guide or slip lock 126 may have a series or plurality of transverse bores 128 formed on each side of a longitudinal central axis of the inner slip lock. The plurality of transverse bores 128 correspond to the plurality of feed through wires 110 and are positioned such that the feedthrough wires may slidingly fit within the bores. In some embodiments, there may also be channels 129 defined with the exterior surfaces of the inner slip lock 126 corresponding to the plurality of transverse bores 128. In certain embodiments, the inner slip lock 126 may be formed with curved longitudinal surfaces or recesses 130a and 130b which run generally parallel to the longitudinal direction of the inner slip lock. As will be explained below, the radii of the curved recesses 130a and 130b may alternate along their respective lengths to match a corresponding change in diameter of the stimulation leads 108a and 108b. In certain embodiments, the inner slip lock 126 may be formed from a compliant material, such as silicone rubber. In other embodiments, the inner slip lock 126 may be formed from a bio-compatible rigid material, such as Bionate® polycarbonate urethane or CarboSil.

The outer seal 104 may partially surround the inner slip lock 126 and, as will be explained below, has an interior orifice (not shown) which generally corresponds to the exterior shape of the inner slip lock. In the illustrative embodiment, the outer seal 104 may have a lead receiving portion 134, a center portion 136, and an end portion 138. Defined within the center portion 136 may be a series of longitudinal curved surfaces 140 which gives the center portion somewhat of an "hour-glass" cross-sectional shape.

Defined within the lead receiving portion 134 are transverse slots or grooves 142a and 142b (only transverse groove 142b is visible in FIG. 2). Similarly, defined within the end portion 138 are transverse grooves 142c and 142d (only transverse groove 142d is visible in FIG. 2). The transverse grooves 142a-142b generally run parallel to the proximal-distal directions. The transverse grooves 142a-142d of the outer seal 104 are sized to slidingly accommodate legs 144a-144d of the clip component 102 (leg 144c is not visible in FIG. 2). In certain embodiments, the clip component 102 may be shaped to correspond to the cross-sectional shape of the center portion 136 of the outer seal 104. Thus, in a first position (as illustrated in FIG. 1), the clip component covers the center portion 136 of the outer seal 104.

In certain embodiments, the lead receiving portion 134 may have strain relief ports 106a-106b which are sized to accept stimulation leads 108a-108b. In certain embodiments, additional annular seals (not shown) may be provided within the lead receiving portion 134 to provide for additional sealing between the outer seal 104 and the stimulation leads 108a and 108b.

Only the proximal ends of the stimulation leads 108a and 108b are shown in FIG. 2. At the proximal end of the stimulation leads 108a and 108b, there may be a plurality of terminals 146a and 146b which are coupled to conductors (not shown) within the leads 108a and 108b. For purposes of illustration only, the leads 108a and 108b are shown with eight terminals. As will be appreciated by those skilled in the art, any number of terminals may be utilized as desired within the leads 108a and 108b. In this illustrative embodiment, the pluralities of terminals 146a and 146b are shown as band or ring terminals. In certain embodiments, the terminals may be formed of biocompatible, conductive materials which do not develop a significant amount of oxide films, such as platinum and platinum-iridium, or other conductive materials, metals or alloys known to those skilled in the art.

Figure 3A:
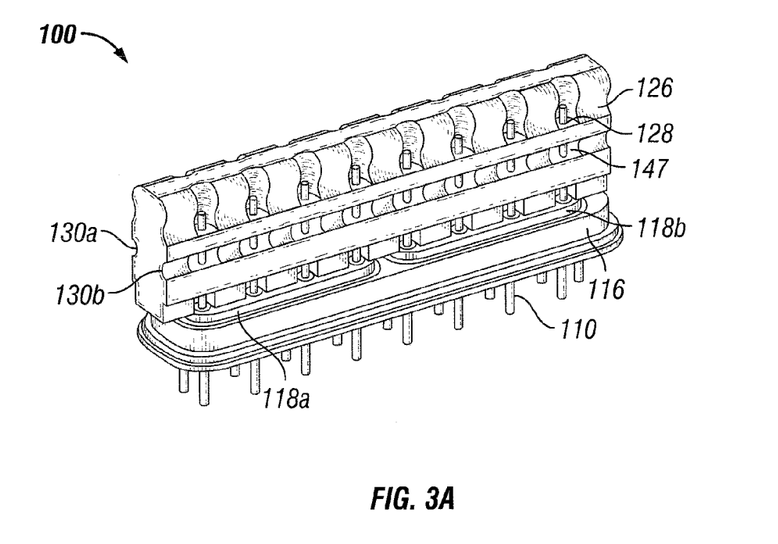
FIG. 3a is a partial isometric view of the header of FIG. 1.

In FIG. 3a, there is illustrated a partial isometric view of the header 100 with the outer seal 104 and the clip component 102 removed for discussion purposes. As illustrated, the inner slip lock 126 is coupled to the supports 118a and 118b which are positioned within the feed-through base 116. The feed-through wires 110 run through the supports 118a and 118b and into the bores 128 of the inner slip lock 126. Once the feed-through wires 110 are positioned within slip lock 126, portions 147 of the feed-through wires 110 are exposed by the intersection of longitudinal side recesses 130a-130b with the bores 128.

Figure 3B:
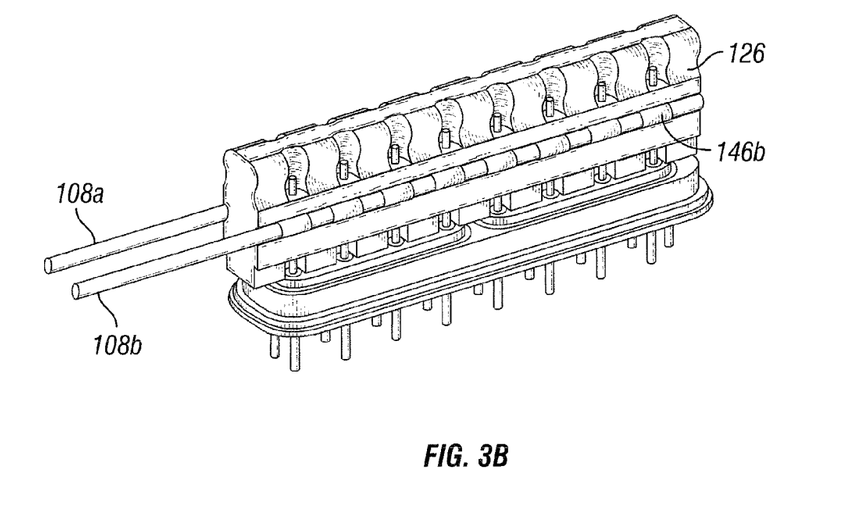
FIG. 3b is a partial isometric view of the header of FIG. 1 coupled to proximal ends of stimulation leads.

FIG. 3b illustrates the stimulation leads 108a-108b coupled to the inner slip lock 126. As one skilled in the art would appreciate, the exposed portions of the feed-through wires 110 contact the terminals 146a and 146b (only the plurality of terminals 146b is shown in FIG. 3b). In certain embodiments, the terminals 146a-146b protrude slightly from the surrounding compliant material of the leads 108a-108b. In such embodiments, the diameter of the side recesses may vary longitudinally to match the varying diameter of the stimulation leads 108a-108b as illustrated in FIG. 3a.

Figure 4A:
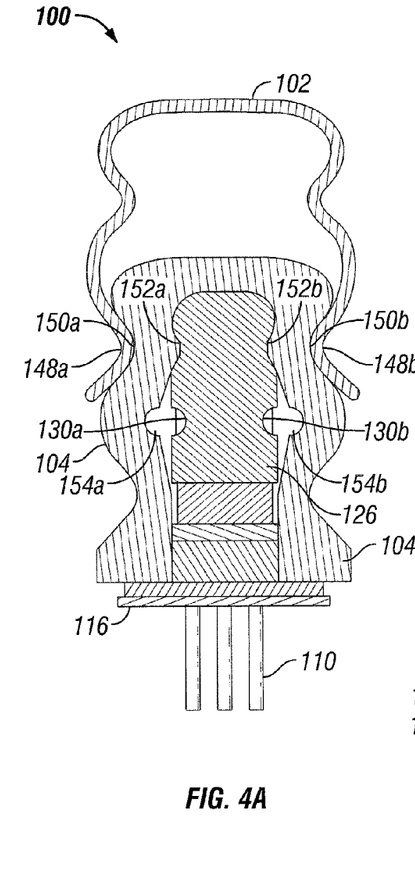
FIG. 4a is a section view of the header of FIG. 1 illustrating an outer cover in a first position.
Figure 4B:
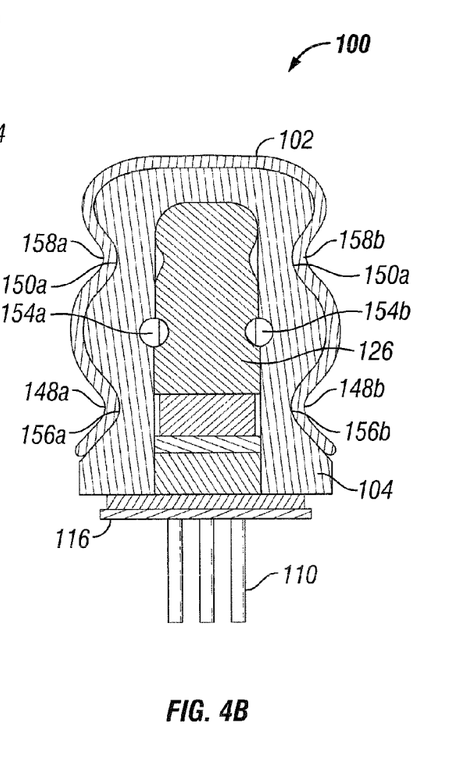
FIG. 4b is a section view of the header of FIG. 1 illustrating an outer cover in a second position.

FIG. 4a is a section view through the header 100 with the clip component 102 coupled to the outer seal 104 in a first or unlocked position. FIG. 4b is a section view through the header 100 with the clip component 102 coupled to the outer seal 104 in a second or locked position. As illustrated in FIGS. 4a and 4b, the feed-through wires 110 extend from distal side of the feedthrough base 116 into the inner slip lock 126. In the unlocked or first position, longitudinal detents 148a-148b of the clip component 102 fit within corresponding curved surfaces 150a-150b of the outer seal 104. As illustrated, voids 154a and 154b are created between opposing curved surfaces of the inner slip lock 126 and the outer seal 104. The proximal end portions of the leads 108a and 108b, may therefore, be inserted into the voids 154a and 154b, respectively.

As illustrated in FIG. 4b, in the second or locked position, the clip component 102 has been moved distally such that longitudinal detents 148a-148b are now positioned within a second pair of curved surfaces 156a-156b of the outer seal 104. In certain embodiments, there may be additional sets of longitudinal detents and corresponding curved surfaces. For instance, as illustrated, there may be longitudinal detents 158a-158b of the clip component 102 positioned against the curved surfaces 150a-150b of the outer seal 104. In certain embodiments, the clip component 102 may be configured so that the longitudinal detents 148a-148b and 158a-158b are biased in an inward direction. Thus, the clip component 102 may provide compression forces to the outer seal 104.

In some embodiments, curved surfaces 152a-152b on the inner slip lock 126 may be configured to cooperate with the biasing action of the longitudinal detents 148a-148b such that the outer seal 104 is forced to moved outwardly away from the side recesses 130a-130b of the inner slip lock 126. Thus, in the first position, such cooperation enlarges the voids 154a-154b and allows for relatively easy insertion of the proximal ends of the stimulation leads 108a-108b into the voids. As illustrated in FIG. 4b, in the locked position, the curved surfaces 152a and 152b no longer cooperate and the voids 154a and 154b are no longer enlarged. So, when the stimulation leads 108a-108b are inserted into the voids 154a-154b and the clip component 102 is in the locked position, the clip component 102 provides compression forces to the outer seal 104, which in turn presses against the terminals 146a-146b of the stimulation leads 108a-108b. Consequently, the terminals 146a-146b are thus pressed against the exposed portions of the feed-through wires 110 such that an electrical connection may be established.

Figure 5A:
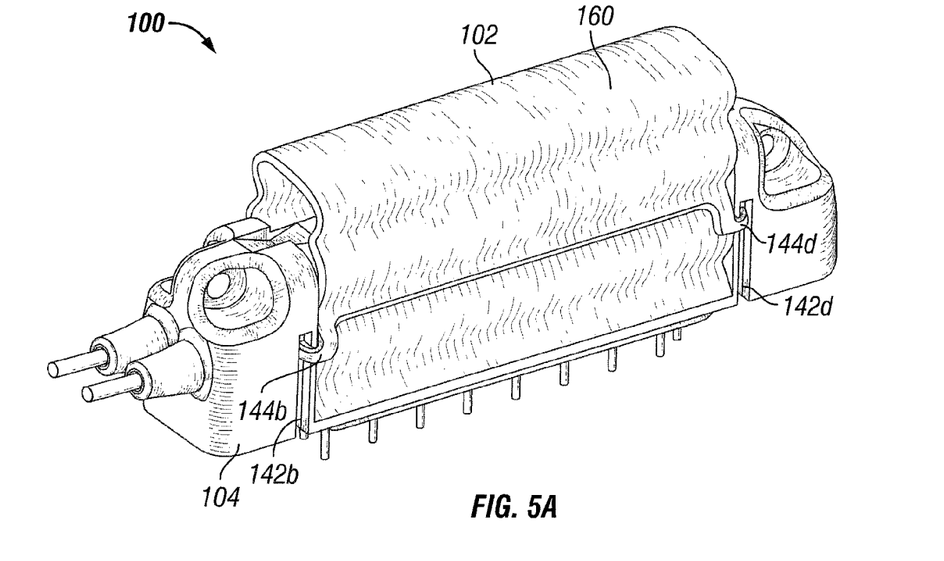
FIG. 5a is an isometric view of the header of FIG. 1 illustrating an outer cover in a first position.
Figure 5B:
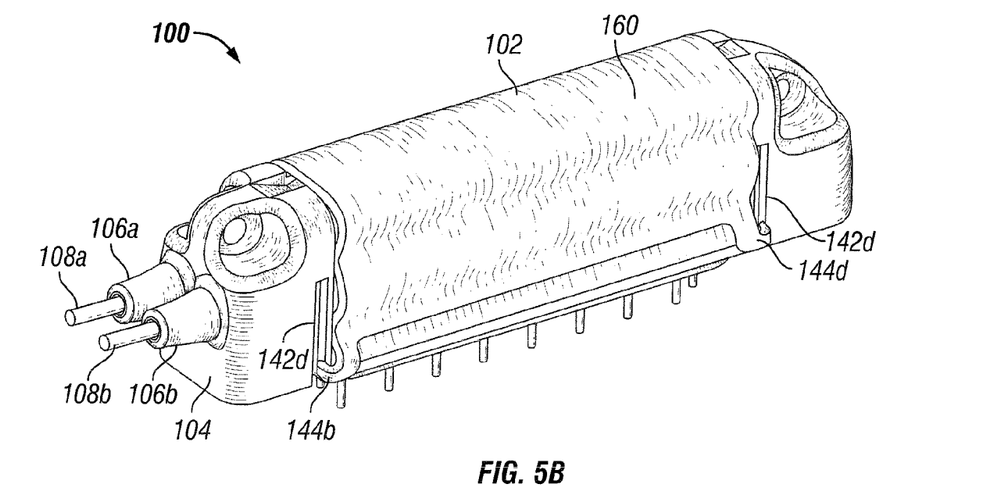
FIG. 5b is an isometric view of the header of FIG. 1 illustrating an outer cover in a second position.

FIG. 5a is an isometric view of the header 100 when the clip component 102 is in the first or unlocked position. FIG. 5b is an isometric view of the header 100 when the clip component 102 is in the second or locked position. In certain embodiments, surgeon or user may move the clip component 102 from the unlocked position illustrated in FIG. 5a to locked position illustrated in FIG. 5b by pressing on a proximal surface 160 of the clip component 102 after the stimulation leads 108a-108b are positioned within the header 100. Thus, in certain embodiments, there may be no need for special tools to lock the clip component 102 in place. As can be seen in FIGS. 5a and 5b, because the legs 144a-144d of the clip component 102 are coupled to the transverse grooves 142a-142d of the outer seal 104, the clip component remains coupled to the outer seal at all times.

When the header 100 is fully assembled and the stimulation leads 108a-108b are placed in header 100 through the strain relief ports 106-106b, the various conductive elements are sealed within the components of header 100. Thus, when an implantable pulse generator with the header 100 is implanted within a patient, the electrical components are sealed and are prevented from contacting bodily fluids.

Referring now to the previous figures, both the feed-through wires 110 and the corresponding terminals 146a-146b may be made from platinum, a platinum-iridium alloy, or other metals that produce non-oxide or low oxide film on their surfaces. With such materials, the contact force to maintain an electrical conductivity may be relatively low (for example, one gram or less). This is in contrast to traditional conductor materials, such as copper, nickel or gold plated alloys which require greater contact forces in order to maintain conductivity. When using materials that do not produce an oxide film, springs and other mechanical compression mechanisms may not be required.

Because the outer seal 104 may be made from silicone rubber or other dielectric materials with fluid properties, the compression of the outer seal 104 by the clip component 102 creates a fluid flow that pushes the terminals 146a-146b against the exposed portions 147 of the feed-through wires 110. Although silicone rubber does exhibit some energy loss, the material can maintains its energy and, thus, may maintain enough compression against the terminals to maintain electrical connectivity between the non-oxide film surfaces of the terminals and feed-through wires 110. In some embodiments, the silicone rubber may also form an effective seal against bodily fluids.

With previous header designs, feedthrough wires are typically electrically coupled to annular electrical connectors. The header structure holds the annular connectors in a fixed arrangement that corresponds to the arrangement of terminals on a stimulation lead. Each connector terminal contacts one of the annular electrical connectors and, thereby, is electrically coupled to the pulse generating circuitry through the feedthrough wires. However, annular connectors take up space which forces the headers to be larger and/or limits the amount of channels that can be used with the pulse generation system. By eliminating the annular connectors as disclosed above, the headers may be made smaller and/or more channels may be used by pulse generation system incorporating various embodiments of the present invention, i.e. 0.050 inch centers, half the current technology or double the connections in the same space/length.

Figure 6:
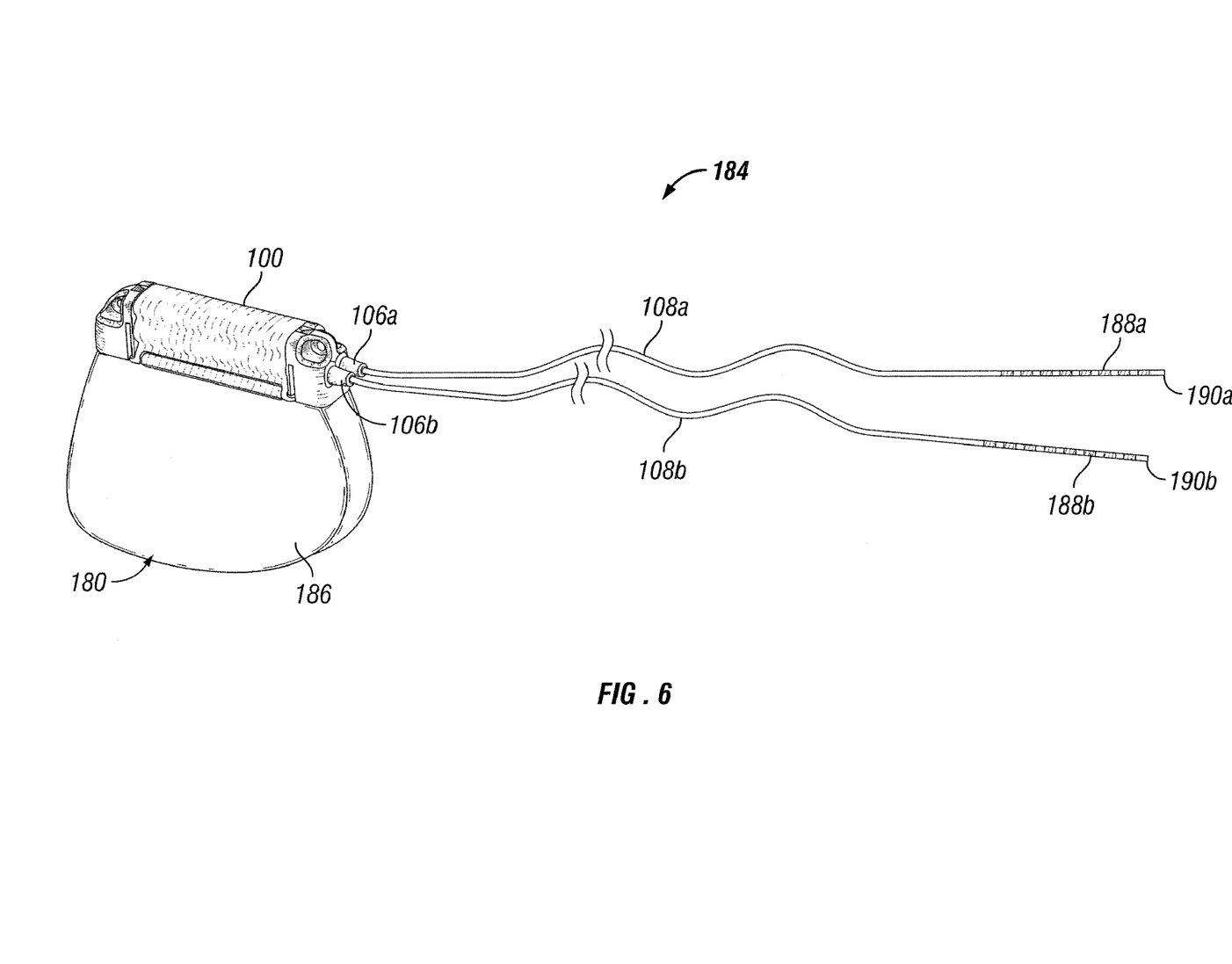
FIG. 6 is a side view of a pulse generation system incorporating the header of FIG. 1.

FIG. 6 illustrates the header 100 connected to a stimulation source, such as an embodiment of an implantable pulse generator (IPG) 180 and stimulation leads 108a and 108b to form a pulse generation system 184. As is well known in the art, the IPG 180 is capable of being implanted within a body (not shown) that is to receive electrical stimulation from implantable pulse generator. In certain embodiments, the IPG 180 may comprise a metallic housing 186 that encloses the pulse generating circuitry, control circuitry, communication circuitry, battery, etc. of the device. An example of pulse generating circuitry is described in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. An embodiment of a microprocessor and associated charge control circuitry for an implantable pulse generator which may be used in certain embodiments is described in U.S. Patent Publication No. 20060259098, entitled "SYSTEMS AND METHODS FOR USE IN PULSE GENERATION," which is incorporated herein by reference. Examples of circuitry for recharging a rechargeable battery of an implantable pulse generator using inductive coupling with an external charging device are described in U.S. patent Ser. No. 11/109,114, entitled "IMPLANTABLE DEVICE AND SYSTEM FOR WIRELESS COMMUNICATION," which is incorporated herein by reference. An example of a commercially available implantable pulse generator that may be adapted to include the header 100 according to some representative embodiments is the EON® implantable pulse generator available from Advanced Neuromodulation Systems, Inc.

In this illustrative example, the stimulation leads 108a and 108b are connected to the implantable pulse generator 180 via the header 100. The leads 108a and 108b may be detached from the pulse generator 180 as desired by applying detaching force and removing proximal end (not shown) of the lead 100 from respective strain relief port 106a-106b. Similarly, the leads 108a and 108b may be connected to the pulse generator 180 by pushing the proximal end into the appropriate strain relief port 106a-106b.

As discussed above, when the system is assembled, the terminals 146a-146b (FIG. 2) are in electrical contact with feed-through wires 110 (FIG. 1). The feed-through wires 110, therefore, connect the terminals to pulse generating circuitry (not shown) within the pulse generator 180. The terminals are themselves in electrical contact with stimulation electrodes 188a and 188b at distal ends 190a and 190b of leads 108a and 108b because conductors (not shown) in the leads 108a and 108b electrically connect the terminals to the stimulation electrodes 188a and 188b.

Thus, the pulse generator 180 may generate and send electrical signals via the leads 108a and 108b to the stimulation electrodes 188a and 188b. In use, the stimulation electrodes 188a and 188b may be placed at a stimulation site (not shown) within a body that is to receive electrical stimulation from the electrical signals. The stimulation site may be, for example, adjacent to one or more nerves in the central nervous system (e.g., spinal cord). The pulse generator 180 may be capable of controlling the electrical signals by varying signal parameters (e.g., intensity, duration, frequency) in response to control signals. In certain embodiments, the pulse generator 180 may programmed by or be in communication with an external programming device (not shown) which supplies the control signals.

Because certain disclosed embodiments rely on fluid or elastomeric forces of the outer seal to maintain an electrical connection, certain connections do not necessarily maintain a relatively large connector force on the leads 108a and 108b. When using certain embodiments, therefore, the leads 108a and 108b may be implanted using a torturous path to anchor the lead in place. The use of a torturous path reduces the potential pull out force after the system has been implanted in a patient, thereby reducing the chances that the lead will separate from the header.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

What is claimed is:

1. A medical implantable pulse generator system comprising:
   a housing enclosing pulse generating circuitry;
   a plurality of feed-through wires coupled to the pulse generating circuitry and extending through the housing;
   a lead having a plurality of terminals;
   a header coupled to the housing, the header comprising:
      a port adapted to receive an end of the lead,
      an inner guide having a plurality of transverse bores positioned to correspond to the plurality of feed-through wires such that the inner guide is slidingly coupled to the plurality of feed-through wires, wherein the inner guide has an exterior longitudinal surface intersecting a portion of each bore of the plurality of transverse bores to create an exposed portion of each feed-through wire of the plurality of feed-through wires, an outer seal having an interior surface sized to support the plurality of terminals such that each terminal is maintained against the exposed portion of a corresponding feed-through wire, and a clip component coupled to the outer seal and biased to compress against the outer seal to create compression forces on the outer seal, and wherein a plurality of longitudinal curved exterior surfaces are defined on the outer seal and a plurality of longitudinal detents are defined by the clip component which are shaped to fit within the plurality of longitudinal curved exterior surfaces.

2. The implantable pulse generator system of claim 1, further comprising:

a second lead having a second plurality of terminals;

a second port defined in the header and adapted to receive an end of the second lead, a second longitudinal surface defined on an opposing side of the inner guide intersecting a portion of the bores of the plurality of transverse bores to create a second exposed portion of certain feed-through wires of the plurality of feed-through wires, and a second interior surface defined within the outer seal sized to support the second plurality of terminals such that each terminal in the second plurality of terminals is maintained against the second exposed portion of a corresponding feed-through wire.

3. The implantable pulse generator system of claim 1 wherein the feed-through wires and the terminals are made from non-oxide film producing conductors.

4. The implantable pulse generator system of claim 1 wherein the feed-through wires and terminals are made from alloys selected from the group consisting of platinum and platinum-iridium.

5. The implantable pulse generator system of claim 1 wherein the outer seal is made from a material able to maintain elastomeric fluid forces on the terminals when the material is under compression forces.

6. The implantable pulse generator of claim 1 wherein the outer seal is made from silicone rubber.

7. The implantable pulse generator system of claim 1, wherein in response to the compression forces created on the outer seal, the outer seal provides compression forces to the terminals to maintain the terminals against the exposed portion of the feed-through wires.

8. The implantable pulse generator system of claim 1, wherein:

the plurality of longitudinal curved exterior surfaces of the inner guide includes a proximal pair of opposing curved surfaces and a distal pair of opposing curved surfaces;

the plurality of longitudinal detents of the clip component includes a proximal pair of opposing detents and a distal pair of opposing detents;

when the clip component is in a first position such that the distal pair of opposing detents are mated with the proximal pair of opposing curved surfaces, voids between the longitudinal surfaces and the outer seal are increased, and when the clip component is in a second position such that the distal pair of opposing detents are mated with the distal pair of opposing curved surface, voids between the recesses and the outer seal are decreased.

9. The implantable pulse generator system of claim 1, further comprising a plurality of lateral grooves defined within an outer surface of the outer seal and a plurality of leg portions coupled to the clip component and slidingly coupled to the lateral grooves such that the clip component can move from a first position to a second position with respect to the outer seal.

10. The implantable pulse generator system of claim 1, wherein:

the terminals are ring terminals having exterior diameters which purchase out from a diameter of compliant material of the lead; and the longitudinal surface of the inner guide is a curved surface having a first diameter along certain longitudinal portions of the curved surface which accommodates the diameter of the ring terminals and having a second diameter along other longitudinal portions of the curved surface which accommodates the diameter of the complaint material.

11. The implantable pulse generator system of claim 1, further comprising:

at least one support having a plurality of lateral bores such that the feed-through wires pass from the interior of the housing through the lateral bores and into the inner guide, a plurality of ring seals positioned between the feed-through wires and the lateral bores, at least one base coupled to the housing having at least one aperture sized to accommodate the at least one support, and at least one seal between the at least one aperture and the at least one support.

12. A header component for a medical implantable pulse generator comprising:

a plurality of feed-through wires adapted to couple to a pulse generating circuitry;

an inner guide having a plurality of bores wherein each bore is positioned to align to the plurality of feed-through wires such that the inner guide is slidingly coupled to the plurality of feed-through wires, wherein the inner guide has an exterior surface intersecting a portion of each bore of the plurality of bores to create an exposed portion of each feed-through wire of the plurality of feed-through wires, an outer seal having a strain relief port for receiving a stimulation lead having a plurality of terminals and a central portion, wherein the central portion has an interior surface sized to support the plurality of terminals against the exposed portions of corresponding feed-through wires when the header is coupled to the stimulation lead, and a clip component fitting over at least a portion of the central portion of the outer seal;

wherein the clip component produces compression forces on the outer seal.

13. The implantable pulse generator system of claim 12 further comprising:

a second strain relief port defined within the outer seal and adapted to receive a second stimulation lead having a second plurality of terminals, a second longitudinal surface defined on an opposing side of the inner guide intersecting a portion of the bores of the plurality of transverse bores to create a second exposed portion of certain feed-through wires of the plurality of feed-through wires, and a second interior surface defined within the outer seal sized to support the second plurality of terminals against the second exposed portions of corresponding feed-through wires when the header is coupled to the second stimulation lead.

14. The header component of claim 12, wherein the feed-through wires and the terminals are made from non-oxide film producing conductors.

15. The header component of claim 12, wherein the outer seal is made from a material able to maintain elastomeric fluid forces on the terminals when the material is under compression forces.

16. The implantable pulse generator of claim 12, wherein the outer seal is made from silicone rubber.

17. The header component of claim 12, further comprising a plurality of longitudinal curved exterior surfaces defined on the outer seal and a plurality of longitudinal detents defined by the clip component which are shaped to fit against the plurality of longitudinal curved exterior surfaces.

18. The header component of claim 17, wherein:
   the plurality of longitudinal curved exterior surfaces includes a proximal pair of opposing curved surfaces and a distal pair of opposing curved surfaces;
   the plurality of longitudinal detents includes a proximal pair of opposing detents and a distal pair of opposing detents;
   when the clip component is in a first position such that the distal pair of opposing detents are mated with the proximal pair of opposing curved surface, voids between the longitudinal curved exterior surfaces and the outer seal are increased, and
   when the clip component is in a second position such that the distal pair of opposing detents are mated with the distal pair of opposing curved surface, voids between the recesses and the outer seal are decreased.

19. The header component of claim 17, further comprising a plurality of lateral grooves defined within an outer surface of the outer seal and a plurality of leg portions coupled to the clip component and slidingly coupled to the lateral grooves such that the clip component can move from a first position to a second position with respect to the outer seal.

20. The header component of claim 12, wherein:
   the terminals are ring terminals having exterior diameters which purchase out from a diameter of compliant material of the lead; and
   the exterior surface is a longitudinal curved surface having a diameter along certain longitudinal portions of the curved surface which accommodates the diameter of the ring terminals and having a second diameter along other longitudinal portions of the curved surface which accommodates the diameter of the complaint material.

21. The header component of claim 12, further comprising:
   at least one support having a plurality of lateral bores such that the feed-through wires pass from the interior of the housing through the lateral bores and into the inner guide,
   a plurality of ring seals positioned between the feed-through wires and the lateral bores,
   at least one base coupled to the housing having at least one aperture sized to accommodate the at least one support, and
   at least one seal between the at least one aperture and the at least one support.

22. A method of assembling an implantable pulse generator system, comprising:
   providing pulse generating circuitry within a housing;
   providing feed-through wires to permit electrical access to the pulse generating circuitry within the housing;
   coupling the feed-through wires to an inner guide to maintain the position of the feed-through wires and to create an exposed portion of each feed-through wire,
   surrounding a portion of the inner guide with an outer seal to create a void proximal to the exposed portion of each feed-through wire,
   inserting terminals of a lead into the void,
   connecting the exposed portions of the feed-through wires to the corresponding terminals, and
   applying compressive forces to the terminals to maintain the terminals against the exposed portions of the feed-through wires;
   wherein the applying compressive forces includes positioning a biasing member over the outer seal to compress the outer seal such that the outer seal applies compressive forces to the terminals;
   wherein the positioning a biasing member includes positioning longitudinal detents of a clip component over longitudinal curved surfaces of the outer sea.

* * * * *